United States Patent
Wallace et al.

(10) Patent No.: US 7,559,933 B2
(45) Date of Patent: *Jul. 14, 2009

(54) ABSORBABLE IMPLANTABLE VASO-OCCLUSIVE MEMBER

(75) Inventors: Michael P. Wallace, Fremont, CA (US); Delilah Yin Hul, Union City, CA (US); Elaine Lee, Sunnyvale, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 641 days.

This patent is subject to a terminal disclaimer.

(21) Appl. No.: 10/423,304

(22) Filed: Apr. 25, 2003

(65) Prior Publication Data

US 2004/0024394 A1 Feb. 5, 2004

Related U.S. Application Data

(63) Continuation of application No. 09/866,887, filed on May 29, 2001, now Pat. No. 6,585,754.

(51) Int. Cl.
*A61F 11/00* (2006.01)

(52) U.S. Cl. .................................... 606/108

(58) Field of Classification Search ................ 44/60.1, 44/60.2, 57.1, 54, 54.1, 44, 71, 55; 606/108, 606/191–200; 623/1.1, 1.11, 1.12, 1.15, 623/1.2

See application file for complete search history.

(56) References Cited

U.S. PATENT DOCUMENTS

| 4,994,069 A | 2/1991 | Ritchart et al. |
| 5,122,136 A | 6/1992 | Guglielmi et al. |
| 5,354,295 A | 10/1994 | Guglielmi et al. |
| 5,536,274 A | 7/1996 | Neuss |
| 5,582,619 A | 12/1996 | Ken et al. .................. 606/191 |
| 5,669,931 A | 9/1997 | Kupiecki |
| 5,690,666 A | 11/1997 | Berenstein et al. |
| 5,690,671 A | 11/1997 | McGurk |
| 5,749,891 A | 5/1998 | Ken et al. |
| 5,749,894 A | 5/1998 | Engelson |
| 5,826,587 A | 10/1998 | Berenstein et al. |
| 5,833,705 A | 11/1998 | Ken et al. .................. 606/191 |
| 5,853,418 A | 12/1998 | Ken et al. .................. 606/191 |
| 5,976,162 A * | 11/1999 | Doan et al. .................. 606/151 |
| 5,980,550 A | 11/1999 | Eder et al. |
| 5,984,929 A * | 11/1999 | Bashiri et al. ............... 606/108 |
| 6,004,338 A | 12/1999 | Ken et al. .................. 606/191 |

(Continued)

FOREIGN PATENT DOCUMENTS

WO   WO 99/44538   9/1999

(Continued)

OTHER PUBLICATIONS

Dondlinger et al., Embolization Materials ed., *Interventional Radiology*, Thieme, N.Y. 295-313 (1990).

(Continued)

*Primary Examiner*—Kevin T Truong
(74) *Attorney, Agent, or Firm*—Robins & Pasternak LLP (57) ABSTRACT

Compositions comprising absorbable implantable vaso-occlusive members are described. Also described are methods of making and using these absorbable vaso-occlusive compositions.

42 Claims, 3 Drawing Sheets

U.S. PATENT DOCUMENTS

| | | | |
|---|---|---|---|
| 6,013,084 A * | 1/2000 | Ken et al. | 606/108 |
| 6,179,857 B1 | 1/2001 | Diaz et al. | 606/194 |
| 6,187,024 B1 | 2/2001 | Boock et al. | 606/191 |
| 6,193,728 B1 | 2/2001 | Ken et al. | 606/108 |
| 6,231,590 B1 | 5/2001 | Slaikeu et al. | 606/200 |
| 6,280,457 B1 * | 8/2001 | Wallace et al. | 606/200 |
| 6,322,576 B1 | 11/2001 | Wallace et al. | 606/191 |
| 6,371,972 B1 | 4/2002 | Wallace et al. | 606/200 |
| 6,425,914 B1 | 7/2002 | Wallace et al. | 623/1.11 |

FOREIGN PATENT DOCUMENTS

| | | |
|---|---|---|
| WO | WO 00/27445 | 5/2000 |
| WO | WO 00/44306 | 8/2000 |
| WO | WO 97/42881 | 11/2007 |

OTHER PUBLICATIONS

Herrera et al., "Histological Changes in the Rat Common Carotid Artery Induced by Aneurysmal Wrapping and Coating Materials," *Neurol. Med. Chir* (*Tokyo*) 39(2):134-139 (1999).

Moringlane et al., "Experimental Aneurysms in the Rabbit: Occlusion by Intrasaccular Injection of Fibrin Sealant," *Surg Neurol.* 28(5):361-366 (1987).

Moringlane et al., "Occlusion of Experimental Artery Aneurysms by Intrasaccular Injection of Fibrin Sealant," *Acta Neurochir Suppl.* (*Wein*) 43:193-197 (1988).

Suga et al., "Fibrin Glue, Aneurysmal Occlusion, Angioplastic Ballon," *No Shinkei Geka* 20(8):865-873 (1992).

Vinters et al., "The Histotoxicity of Cyanoacrylates," Neuroradiology 27:279-291 (1995).

* cited by examiner

ABSORBABLE IMPLANTABLE VASO-OCCLUSIVE MEMBER

This application is a continuation of patent application Ser. No. 09/866,887 filed May 29, 2001, now U.S. Pat. No. 6,585,754, from which priority is claimed under 35 U.S.C. § 120 and which is incorporated herein by reference in its entirety.

FIELD OF THE INVENTION

Compositions and methods for repair of aneurysms are described. In particular, completely or almost completely absorbable vaso-occlusive members are disclosed, as are methods of making and using these members.

BACKGROUND

An aneurysm is a dilation of a blood vessel (similar to a balloon) that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. (See, e.g., U.S. Pat. No. 4,994,069 to Ritchart et al.) Other less stiff helically coiled devices have been described, as well as those involving woven braids.

U.S. Pat. No. 5,354,295 and its parent, U.S. Pat. No. 5,122,136, both to Guglielmi et al., describe an electrolytically detachable embolic device. Vaso-occlusive coils having little or no inherent secondary shape have also been described. For instance, co-owned U.S. Pat. Nos. 5,690,666 and 5,826,587 by Berenstein et al., describes coils having little or no shape after introduction into the vascular space.

Attempts to increase thrombogenicity of metal coils have also been attempted, for example by modifying the surface of the coil. WO 99/44538 discloses use of GDC coils coated with biodegradable polymers or proteins. U.S. Pat. No. 5,669,931 to Kupiecki discloses coils that may be filed or coated with thrombotic or medicinal material. U.S. Pat. No. 5,749,894 to Engleson discloses polymer coated vaso-occlusion devices. U.S. Pat. No. 5,690,671 to McGurk discloses an embolic element which may include a coating, such as collagen, on the filament surface. U.S. Pat. No. 5,536,274 to Neuss shows spiral implants, some of which are coated with metal particles, silicone, PTFE, rubber latices, or polymers. U.S. Pat. No. 5,980,550 describes a vaso-occlusive device having a bioactive inner coating and a water-soluble outer coating. Co-owned WO/027445, titled "Bioactive Coating for Vaso-occlusive Devices," describes vaso-occlusive devices coated with a collagen-based material and, additionally, describes the use of a tie-layer between the device and the collagen-based coating.

Liquid embolics, such as cyanoacrylate glues and fibrin sealants, have also been used in animal and human subjects. See, e.g., Interventional Radiology, Dandlinger et al, ed., Thieme, N.Y., 1990:295-313; Suga et al. (1992) *No Shinkei Geka* 20(8):865-873; Moringlane et al. (1987) *Surg Neurol* 28(5):361-366; Moringlane et al. (1988) *Acta Neurochir Suppl. (Wein)* 43:193-197. Of these liquid embolics, cyanoacrylate glues are the only liquid embolics currently available to neurosurgeons. However, chronic inflammation is typically seen with cyanoacrylate treatments (Herrera et al. (1999) *Neurol Med Chir (Tokyo)* 39(2):134-139) and the degradation product, formaldehyde, is highly toxic to the neighboring tissues. See, Vinters et al (1995) *Neuroradiology* 27:279-291. Another disadvantage of cyanoacrylate materials is that the polymer will adhere both to the blood vessel and to the tip of the catheter. Thus physicians must retract the catheter immediately after injection of the cyanoacrylate embolic material or risk adhesion of the cyanoacrylate and the catheter to the vessel.

WO 00/44306 discloses endovascular apparatuses comprising an at least partially absorbable polymeric or protein coil and a placement device.

None of these documents describe vaso-occlusive members having the characteristics described herein or methods of making such members.

SUMMARY OF THE INVENTION

Thus, this invention includes novel occlusive compositions as well as methods of using and making these compositions.

In one aspect, the invention includes an absorbable vaso-occlusive member comprising: (i) an absorbable material; and (ii) one or more stretch-resistant members fixedly attached to at least two locations of the absorbable material. Non-limiting examples of suitable absorbable materials include polyglycolic acid (PGA), poly-glycolic/poly-L-lactic acid co-polymers, polycaprolactone, polyhydroxybutyrate/hydroxyvalerate copolymers, poly-L-lactide, polydioxanone, polycarbonates, polyanhydrides, collagen, elastin, fibrinogen, fibronectin, vitronectin, laminin, gelatin and combinations thereof.

The vaso-occlusive members described herein can have any three-dimensional shape, including, for example, J-shaped, straight, cylindrical, spherical, tube-like, and helical coil. In certain embodiments, for example where the vaso-occlusive member is configured as a helical coil having a plurality of helical winds, a first end, a second end and lumen between said first and second ends, the stretch-resistant member extends through said lumen of the coil and is attached to said first and second ends. Alternatively, the stretch-resistant member can be threaded through holes, perforations or winds of the three-dimensional member (e.g., threaded through winds of a coil or through perforations of a tube). Furthermore, in any of the vaso-occlusive members described the stretch-resistant member can be attached to the interior or, alternatively, exterior of the members (e.g., helical coil or tube).

In certain embodiments, the stretch-resistant member is non-absorbable. In other embodiments, the stretch-resistant member is absorbable. For example, absorbable stretch-resistant members can be separately added elements or, alternatively, the stretch-resistant member(s) can be formed by modifying the absorbable material, for example by heating or soldering selected locations of the absorbable vaso-occlusive member, e.g., by soldering lines on the exterior or interior of a tube-shaped member or by heating or soldering one or more winds of a helically shaped member to connect at least two of said helical winds. In certain aspects, the stretch-resistant member comprises a mono-filament, for example polypropylene. In other embodiments, the stretch-resistant member is a multi-filament.

Any of the vaso-occlusive members described herein can further comprise a deployment tip, for example attached to at least one of the first end and second end of the member (e.g., coil or tube shape). The deployment tip can be, for example, an electrolytically detachable end adapted to detach from a pusher by imposition of a current on said pusher. Further, any of the vaso-occlusive members described herein can further comprise a radio-opaque material (for example powdered tantalum, powdered tungsten, bismuth oxide, and barium sulfate) and/or a bioactive material.

In yet another aspect, a method for producing a vaso-occlusive member is described comprising the steps of (i) preparing a generally linear primary element comprising an absorbable material; (ii) winding said primary element onto a mandrel; and (iii) heating said mandrel and said primary element to produce said three dimensional member (e.g, a 15 minute heating step at approximately 165° C.). The vaso-occlusive member can have a variety of three-dimensional configurations including, for example, a helical coil configuration, a conical shape or a spiral shape. Further, any suitable mandrel can be used, for example, a stainless steel mandrel.

In yet another aspect, the invention includes a method for producing a vaso-occlusive member comprising the steps of preparing a tube-like structure comprising an absorbable material, for example by micro-machining.

In any of the methods described herein, the absorbable material can be, for example, polyglygolic acid (PGA), poly-glycolic/poly-L-lactic acid co-polymers, polycaprolactone, polyhydroxybutyrate/hydroxyvalerate copolymers, poly-L-lactide, polydioxanone, polycarbonates, polyanhydrides, collagen, elastin, fibrinogen, fibronectin, vitronectin, laminin, gelatin and combinations thereof.

Any of the methods described herein can further include the step of fixedly attaching one or more stretch-resistant members to two or more locations on the vaso-occlusive member, for example by knotting, heating or soldering the stretch-resistant member to the device or by heating, soldering, or plasticizing portions of the device to each other. In any of these methods, the stretch-resistant member can be either absorbable or non-absorbable. Furthermore, the stretch-resistant member can be a mono-filament, for example, polypropylene or a multi-filament.

In any of the methods described herein, the vaso-occlusive member can further comprise one or more radio-opaque material, for example, powdered tantalum, powdered tungsten, bismuth oxide, and barium sulfate and/or one or more bioactive materials.

These and other embodiments of the subject invention will readily occur to those of skill in the art in light of the disclosure herein.

DESCRIPTION OF THE INVENTION

Occlusive (e.g., embolic) compositions are described. The embolic compositions include, for example, completely or substantially absorbable vaso-occlusive members. Additional materials may also be used in these embolic compositions. The compositions described herein find use in vascular and neurovascular indications and are particularly useful in treating aneurysms, for example small-diameter, curved or otherwise difficult to access vasculature, for example cerebral aneurysms. Methods of making and using these vaso-occlusive members also an aspects of this invention.

Advantages of the present invention include, but are not limited to, (i) promoting healing of aneurysms using complete (or virtually complete) absorption rather than partial absorption of the embolic material; (ii) reducing or eliminating painful mass effect associated with some aneurysms or use of some vaso-occlusive devices; (iii) encouraging greater tissue ingrowth in the aneurysm due to the absorbable nature of the member, which in turn results in (iv) more stable aneurysms.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to "a filament" includes a mixture of two or more such filaments and the like.

In one aspect, the invention includes absorbable material useful in occluding aneurysms. The term "absorbable" refers to any agent which, over time, is no longer identifiable at the site of application in the form it was injected, for example having been removed via degradation, metabolism, dissolving or any passive or active removal procedure. It will be understood that in certain embodiments, not all of the material is absorbable. Thus, the term includes both complete and substantially complete absorption over a period of time ranging from hours to months. Preferably, 80-100% (or any value therebetween) of the material is absorbed; even more preferably 90 to 100% (or any value therebetween) of the material is absorbed and most preferably 100% of the material is absorbed over time. Thus, absorbable vaso-occlusive members are to be contrasted with hybrid devices made up of both absorbable material and non-absorbable material, such as nitinol, in which less than substantially all of the device is absorbed over time.

Thus, described herein are novel structures and novel methods of manufacturing absorbable vaso-occlusive members. Absorbable materials suitable for use in the compositions and methods of the present invention include, but are not limited to, polymers and proteins. Suitable polymers include, for example, polyglygolic acid (PGA), poly-glycolic/poly-L-lactic acid co-polymers, polycaprolactone, polyhydroxybutyrate/hydroxyvalerate copolymers, poly-L-lactide, polydioxanone, polycarbonates, and polyanhydrides. Non-limiting examples of bioabsorbable proteins include collagen, elastin, fibrinogen, fibronectin, vitronectin, laminin and gelatin. Many of these materials are commercially available. Fibrin-containing compositions are commercially available, for example from Baxter. Collagen containing compositions are commercially available, for example from Cohesion Technologies, Inc., Palo Alto, Calif. Fibrinogen-containing compositions are described, for example, in U.S.

Pat. Nos. 6,168,788 and 5,290,552. As will be readily apparent, absorbable materials can be used alone or in any combination with each other. The absorbable material may be in the form of a mono-filament or, alternatively, a multi-filament strands.

Furthermore, the absorbable materials can also be used in combination with additional components. For example, lubricious materials (e.g., hydrophilic) materials may be used to coat the member to help facilitate delivery. One or more bioactive materials may also be included. The term "bioactive" refers to any agent which exhibits effects in vivo, for example a thrombotic agent, a therapeutic agent or the like. Non-limiting examples of bioactive materials include cytokines; extracellular matrix molecules (e.g. collagen); trace metals (e.g., copper); and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Non-limiting examples of cytokines which may be used alone or in combination in the practice of the present invention include, basic fibroblast growth factor (bFGF), platelet derived growth factor (PDGF), vascular endothelial growth factor (VEGF), transforming growth factor beta (TGF-$\beta$) and the like. Cytokines, extracellular matrix molecules and thrombus stabilizing molecules (e.g., Factor XIII, PAI-1, etc.) are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequence of many of these molecules are also available, for example, from the GenBank database. Thus, it is intended that the invention include use of DNA or RNA encoding any of the bioactive molecules. Furthermore, it is intended, although not always explicitly stated, that molecules having similar biological activity as wild-type or purified cytokines, extracellular matrix molecules and thrombus-stabilizing proteins (e.g., recombinantly produced or mutants thereof) and nucleic acid encoding these molecules are intended to be used within the spirit and scope of the invention. Further, the amount and concentration of liquid embolic and/or other bioactive materials useful in the practice of the invention can be readily determined by a skilled operator and it will be understood that any combination of materials, concentration or dosage can be used, so long as it is not harmful to the subject.

It also may be desirable to include one or more radio-opaque materials for use in visualizing the members in situ. Thus, the absorbable members may be coated or mixed with radio-opaque materials such as metals (e.g. tantalum, gold or platinum particles); barium sulfate; bismuth subcarbonate; or the like.

Figure 1:
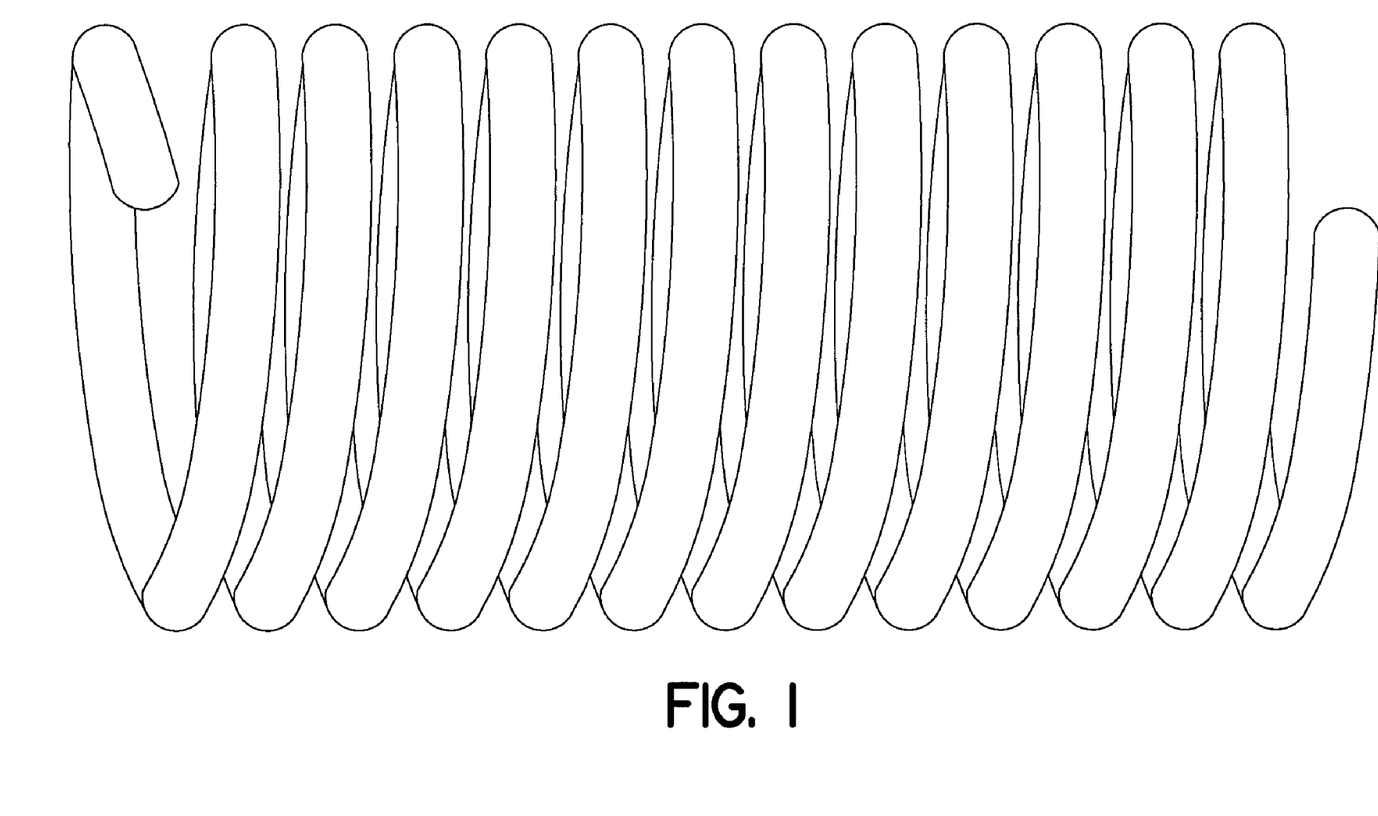
FIG. 1 depicts an exemplary absorbable vaso-occlusive member of the present invention having a helical configuration.
Figure 2:
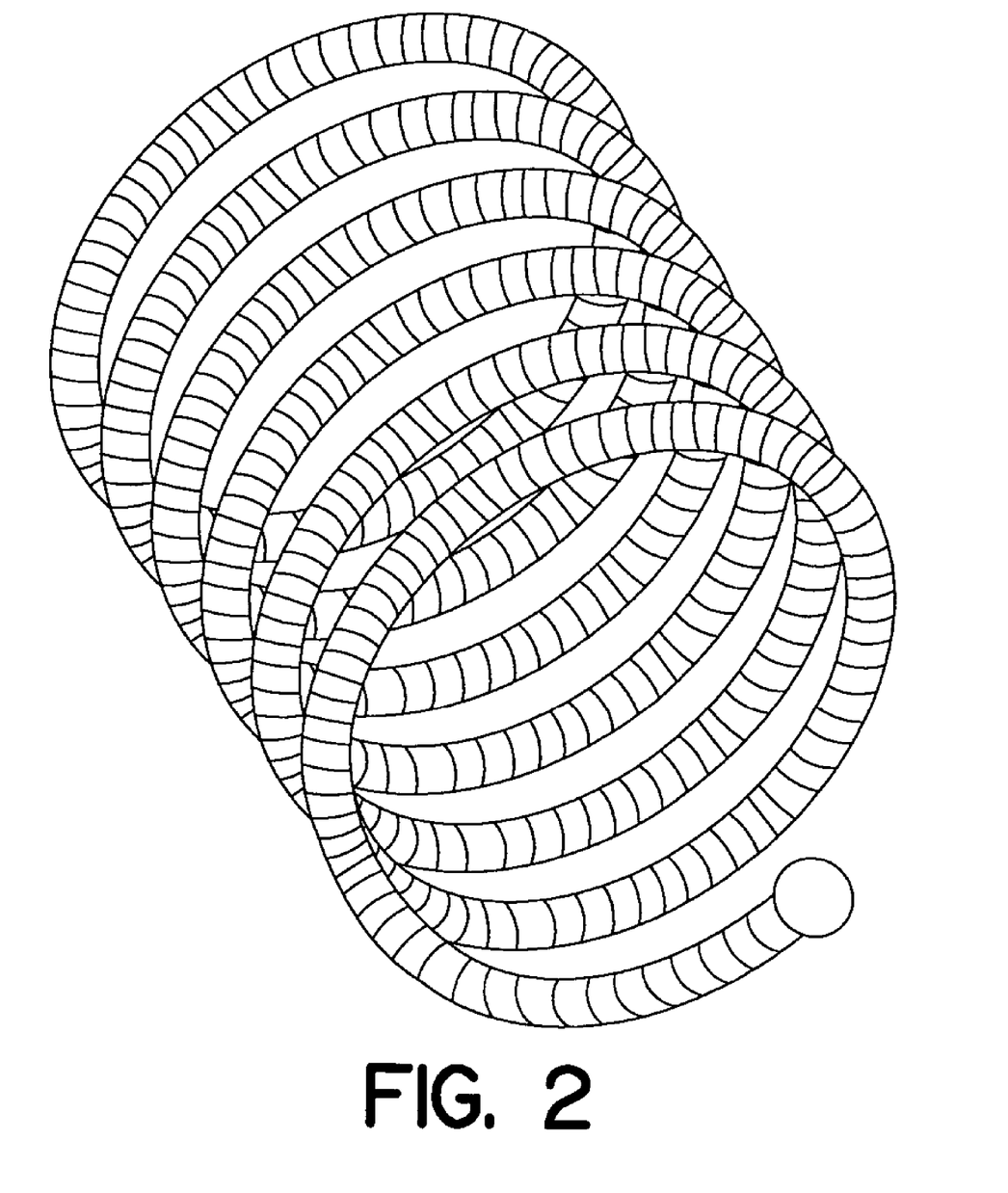
FIG. 2 depicts an exemplary stretch-resistant and absorbable vaso-occlusive member according to the present invention.
Figure 3:
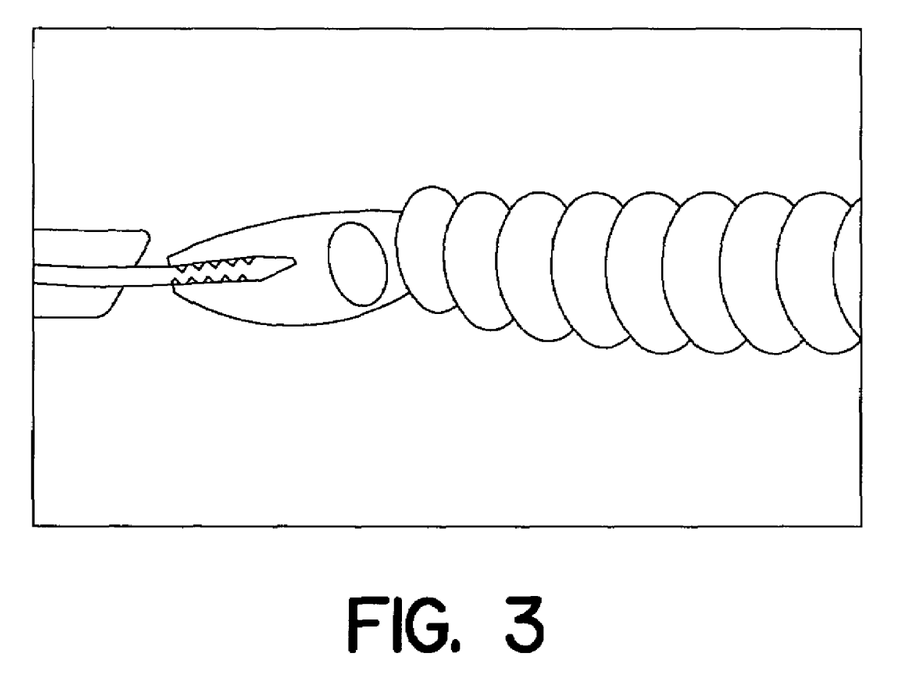
FIG. 3 depicts an electrolytic GDC-type detachment junction.

The absorbable vaso-occlusive members may take on a variety of shapes (e.g., configurations). FIG. 1 shows one embodiment of the present invention in which the absorbable material takes on a helical shape upon deployment. Braided absorbable vaso-occlusive members are also included within the scope of the present invention. For example, a multi-lead braid can be made by braiding absorbable material(s) around a removable core wire. Additionally, the vaso-occlusive member may take the form of a tube-like structure, with or without one or more perforations or holes. It is further within the scope of this invention that the absorbable vaso-occlusive device comprise shapes or structures other than coils, braids and tubes, for examples, J-shaped, straight, cylindrical, spheres, ellipses, spirals, figure-8 shapes, etc. Any of the vaso-occlusive members described herein, for example tube-like structures, may be partially or fully micro-machined.

In certain embodiments, the vaso-occlusive members are "stretch-resistant." (See, e.g., U.S. Pat. Nos. 6,193,728; 6,013,084; 6,004,338; 5,853,418; and 5,833,705 for a description of non-absorbable stretch-resistant devices, all of which are hereby incorporated by reference in their entireties). Typically, stretch-resistant devices include a stretch-resistant member fixedly attached to two or more points on the device. The stretch-resistant member may be absorbable or, alternatively, may be a substantially non-absorbed material such as polypropylene. Both absorbable and non-absorbable materials (e.g., suture materials) are commonly available and can be used in the compositions and methods described herein.

The stretch-resistant member can be fixed to the absorbable device in one or more locations, for example near the ends, on the inside or outside surface or combinations thereof. Furthermore, the stretch-resistant member can be attached by any means, including, but not limited to, heating (e.g. soldering), threading, knotting, plasticizing, etc. Additionally, in certain embodiments, the stretch-resistant member(s) are formed by modifying the absorbable material so as to connect selected regions of the vaso-occlusive member to one another. For example, two or more individual winds of a helically shaped absorbable vaso-occlusive device may be heated, soldered or otherwise treated so that they are connected or otherwise fused, thereby forming one or more stretch-resistant members (and a stretch-resistant device). Similarly, one or more modified regions may be formed by heating, soldering, plasticizing or the like, selected areas of a tube-shaped absorbable structure to make it stretch-resistant. It will be apparent that the modified regions may be of any shape, for example lines, curves, etc, and may be parallel or at angles to each other and/or parallel or at various angles to the longitudinal axis of the tube. Any of the modifications to the absorbable material that render the device stretch-resistant may be on the interior and/or exterior surfaces of the vaso-occlusive member.

Methods of Manufacture

Methods of making the absorbable vaso-occlusive members described are also provided. The vaso-occlusive members described herein are typically formed by winding the absorbable material into a first helix, typically a coil; the first helix is then wound into a secondary form. Typically, the secondary form is one which, when ejected from a delivery catheter, forms a three-dimensional shape to substantially fill the body cavity. Desirably, the vaso-occlusive member is of a size and shape suitable for fitting snugly within a vascular cavity (e.g., an aneurysm, or perhaps, a fistula).

Primary and secondary forms are generally provided by shaping the absorbable material, for example, winding the material on a mandrel or a removable core wire. Vaso-occlusive members according to the present invention can also be formed by winding a single or multi-lead absorbable material (s) around a removable core wire. Suitable winding mandrels, for winding both primary and secondary configurations, may be a variety of shapes (e.g., cylindrical, square, spherical, circular, rectangular, etc.) and may be solid or hollow. Some exemplary shapes of mandrels are shown in co-owned U.S. Pat. No. 5,957,948 to Mariant et al. As noted above, the winding mandrel is typically of sufficient heat resistance to allow a moderate annealing step. The mandrel may be made of stainless steel or other metallic material, alumina, zirconia or the like. Composite mandrels (e.g., composites of conductive and non-conductive materials) described in co-owned U.S. Ser. No. 09/637,470 may also be employed.

Further, it is usually desirable to ensure that the primary coil does not unravel, for example by taping, clipping or otherwise attaching the primary coil (e.g., the ends) to the mandrel. The primary coil-mandrel complex is preferably annealed at a temperature between about 50° and 200° C., more preferably between about 75° and 150° C. and even more preferably around 100° C. The time of annealing can vary from seconds to hours. Annealing may be omitted or performed at different temperatures, so long as the coil retains its shape after winding and can be readily removed from the mandrel.

In certain embodiments, the primary configuration is then wound into a secondary configuration on a mandrel. Again, suitable mandrels can be selected by the operator based on the desired size and shape of the resulting vaso-occlusive member. As with procedures for winding the primary configuration, clips or other securing means (e.g., tape) may be used to secure the vaso-occlusive member to the selected mandrel. The secondary coil-mandrel complex is preferably annealed, for example at a temperature between about 100° and 500° C., more preferably between about 100° and 200° C. and even more preferably between about 160 and 170° C. The time of annealing can vary from seconds to hours. The absorbable material may be wound or braided on the mandrel or other support structure manually. Alternatively, winding machines are commercially available and can be programmed to wind the absorbable material as desired. An exemplary helical secondary configuration is shown in FIG. 1.

As noted above, the devices described herein may also assume a variety of shapes upon deployment. An exemplary helical secondary configuration is shown in FIG. 1. Other shapes include, but are not limited to, spherical, ovoid, Figure-8, conical, spiral, random three-dimensional shapes and the like.

In certain embodiments, the absorbable device is made by injection-molding and/or micro-machining. (See, e.g., co-owned U.S. patent application entitled "Injection Molded Vaso-Occlusive Elements," filed even date herewith).

In embodiments that include a stretch-resistant member, the stretch-resistant member can be attached to the vaso-occlusive member in any number of ways including but not limited to, looping or threading of the stretch-resistant member through the turns and/or lumen (if the vaso-occlusive member is of a configuration to permit such looping or threading); heating, soldering; plasticizing or solvating the junction points to soften the material at the junction and, subsequently allowing re-solidification; or combinations of one or more of these procedures. For example, when the absorbable device is of a helical configuration or a tube with perforations, the stretch-resistant member may be threaded through the coil winds or through the perforations. It will also be apparent that the stretch-resistant member may be attached by any of these methods to the interior or exterior surface of the device. As noted above, the stretch-resistant number may be either absorbable or non-absorbable. In certain embodiments, the stretch-resistant member(s) are formed from the absorbable material itself, for example, by heating or plasticizing selected regions of the device to fuse or otherwise connect the regions and make the device stretch-resistant. In view of the teachings herein, those skilled in the art will be readily able to determine which regions of the absorbable material should be modified and how the connections should be made.

Additional materials (e.g., bioactive materials and/or radio-opaque materials) can be made included using any conventional techniques, for example by dipping, coating or soaking the absorbable vaso-occlusive member in the additional material(s). Other techniques as known in the art, such as shrink-wrapping, spraying may also be used. In additional, the additional material(s) may be injected into the interior lumen and/or exterior surfaces of the absorbable member.

Methods of Use

The embolic compositions described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place absorbable vaso-occlusive member at the target site but yet with a sufficient portion of the distal end of the delivery mechanism protruding from the distal end of the catheter to enable detachment of the implantable vaso-occlusive member. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, the liquid embolics and/or occlusive members described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g., mechanical devices, absorbable vaso-occlusive members and/or liquid embolics and bioactive materials) which cause formation of an emboli and, at some later time, is at least partially replaced by neovascularized collagenous material formed around the implanted vaso-occlusive members.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the absorbable vaso-occlusive member at the distal end, is advanced through the catheter.

Once the selected site has been reached, the absorbable vaso-occlusive member is extruded, for example by loading onto a pusher wire. Preferably, the vaso-occlusive member is loaded onto the pusher wire via a mechanically or electrolytically cleavable junction (e.g., a GDC-type junction that can be severed by application of heat, electrolysis, electrodynamic activation or other means). Additionally, the vaso-occlusive member can be designed to include multiple detachment points, as described in co-owned U.S. patent application titled "LIGHT-ACTIVATED MULTI-POINT DETACHMENT MECHANISM". They are held in place by gravity, shape, size, volume, magnetic field or combinations thereof. As noted above, the order in which the components of the vaso-occlusive composition are released from the catheter is not critical to the practice of the invention and can be determined by the operator.

EXAMPLES

Example 1

Primary Configuration

We produced a series of primary coils having made from absorbable PGA materials from 0.0055" PGA mono-filament (0.0055", Biogeneral Fiber Technology, Batch # 2005-154) wound over a 0.007" OD stainless steel mandrel, with or without PTFE tubing. The primary coils were wound using the procedures discussed above and annealed at a temperature of 100° C. for 10 minutes. Well-shaped, easy to remove primary coils were formed.

Example 2

Secondary Configuration

A series of absorbable vaso-occlusive members having secondary configurations were also produced. Primary coils were produced essentially as described in Example 1 and then the primary coil was wound into a secondary configuration, with or without PTFE tubing, around a 0.004" OD stainless steel mandrel. The secondary shapes were annealed at a temperature of 165° C. for between about 15 and 30 minutes. Absorbable vaso-occlusive members with secondary configurations, such as those shown in the Figures, were formed.

Example 3

Stretch-Resistant Configurations

Absorbable vaso-occlusive members with secondary configurations produced as described in Example 2 were then modified to be stretch-resistant. In particular, the coil was modified so that suture material (non-absorbable, polypropylene mono-filament suture) was attached by threading and/or by soldering at two more locations of the secondary configuration. Subsequently, the suture-containing absorbable vaso-occlusive member was attached to a pusher wire for deployment.

Modifications of the procedure and vaso-occlusive members described above, and the methods of using them in keeping with this invention will be apparent to those having skill in this mechanical and surgical art. These variations are intended to be within the scope of the claims that follow.

What is claimed is:

1. A vaso-occlusive member comprising:
   (i) an absorbable material having a three-dimensional configuration, the three-dimensional configuration having two ends and a longitudinal exterior surface extending between the two ends, wherein the absorbable material is detachably connected to a core wire; and
   (ii) one or more stretch-resistant members fixedly attached to at least two locations of the absorbable material, wherein one or more of the stretch-resistant members extend over most or all of the longitudinal exterior surface of the absorbable material.

2. The vaso-occlusive member of claim 1, wherein the vaso-occlusive member has a configuration selected from the group consisting of J-shaped, straight, cylindrical, spherical, tube-like, and helical coil.

3. The vaso-occlusive member of claim 2, wherein the absorbable material is configured as a helical coil having a plurality of helical winds, a first end, a second end and lumen between said first and second ends.

4. The vaso-occlusive member of claim 3, wherein the stretch-resistant member is threaded through the winds of said coil.

5. The vaso-occlusive member of claim 3, wherein the stretch-resistant member is attached to the interior or exterior of the helical coil.

6. The vaso-occlusive member of claim 1, wherein the stretch-resistant member is absorbable.

7. The vaso-occlusive member of claim 1, wherein the stretch-resistant member is non-absorbable.

8. The vaso-occlusive member of claim 1, wherein the absorbable material is selected from the group consisting of polyglygolic acid (PGA), poly-glycolic/poly-L-lactic acid co-polymers, polycaprolactone, polyhydroxybutyrate/hydroxyvalerate copolymers, poly-L-lactide, polydioxanone, polycarbonates, polyanhydrides, collagen, elastin, fibrinogen, fibronectin, vitronectin, laminin, gelatin and combinations thereof.

9. The vaso-occlusive member of claim 1, wherein the stretch-resistant member is a mono-filament.

10. The vaso-occlusive member of claim 9, wherein the mono-filament comprises polypropylene.

11. The vaso-occlusive member of claim 1, wherein the stretch-resistant member is a multi-filament.

12. The vaso-occlusive member of claim 1, further comprising a deployment tip.

13. The vaso-occlusive member of claim 12, wherein the deployment tip comprises an electrolytically detachable end adapted to detach from a pusher by imposition of a current on said pusher.

14. The vaso-occlusive member of claim 1, further comprising a radio-opaque material.

15. The method of claim 14, wherein the radio-opaque material is selected from the group consisting of powdered tantalum, powdered tungsten, bismuth oxide, and barium sulfate.

16. The vaso-occlusive member of claim 1, further comprising a bioactive material.

17. A method for producing a vaso-occlusive member according to claim 1, the method comprising the steps of:
   (i) preparing a generally linear primary element comprising an absorbable material;
   (ii) winding said primary element onto a mandrel;
   (iii) heating said mandrel and said primary element to produce a three-dimensional member; and
   (iv) fixedly attaching one or more stretch-resistant members to two or more locations of the three-dimensional member such that one or more of the stretch-resistant members extend over most or all of the longitudinal exterior surface of the three-dimensional member.

18. The method of claim 17, wherein the vaso-occlusive member has a three-dimensional configuration comprising a helical coil.

19. The method of claim 17, wherein the vaso-occlusive member has a three-dimensional configuration comprising a conical or spiral shape.

20. The method of claim 17, wherein step (iii) comprises an approximately 15 minute heating step at approximately 165° C.

21. The method of claim 17, wherein the mandrel comprises stainless steel.

22. The method of claim 17, wherein the vaso-occlusive member further comprises at least one radio-opaque material.

23. The method of claim 22, wherein the radio-opaque material is selected from the group consisting of powdered tantalum, powdered tungsten, bismuth oxide, and barium sulfate.

24. The method of claim 17, wherein the vaso-occlusive member further comprises at least one bioactive material.

25. The vaso-occlusive device of claim 1, further comprising a lubricious material.

26. The vaso-occlusive device of claim 25, wherein the lubricious material is coated onto the device.

27. A vaso-occlusive member comprising
   (i) an absorbable material configured as a tube; and
   (ii) one or more stretch-resistant members fixedly attached to at least two locations of the tube, wherein one or more of the stretch-resistant members extend over most or all of the longitudinal exterior surface of the tube.

28. The vaso-occlusive member of claim 27, wherein the tube comprises a plurality of perforations therein.

29. The vaso-occlusive member of claim 28, wherein the stretch-resistant member is threaded through at least two of said perforations.

30. The vaso-occlusive member of claim 27, wherein the stretch-resistant member is attached to the interior or exterior of the tube.

31. A method for producing a vaso-occlusive member according to claim 27, the method comprising the steps of
   (i) preparing a tube-like structure comprising an absorbable material; and
   (ii) fixedly attaching one or more stretch-resistant members to two or more locations of the tube.

32. The method of claim 31, wherein the preparing comprises micro-machining.

33. The method of claim 17 or claim 31, wherein the absorbable material is selected from the group consisting of polyglygolic acid (PGA), poly-glycolic/poly-L-lactic acid co-polymers, polycaprolactone, polyhydroxybutyrate/hydroxyvalerate copolymers, poly-L-lactide, polydioxanone, polycarbonates, polyanhydrides, collagen, elastin, fibrinogen, fibronectin, vitronectin, laminin, gelatin and combinations thereof.

34. The method of claim 17 or claim 31, further comprising the step of connecting two or more locations of the vaso-occlusive member to form one or more stretch-resistant members.

35. The method of claim 34, wherein the connections are formed by heating or soldering the two or more locations to one another.

36. The method of claim 34, wherein the stretch-resistant member is absorbable.

37. The method of claim 34, wherein the stretch-resistant member is non-absorbable.

38. The method of claim 34, wherein the stretch-resistant member is a mono-filament.

39. The method of claim 38, wherein the mono-filament comprises polypropylene.

40. The method of claim 34, wherein the stretch-resistant member is a multi-filament.

41. The method of claim 34, wherein the stretch-resistant member is knotted to the vaso-occlusive member.

42. The method of claim 34, wherein the stretch-resistant member is soldered to the vaso-occlusive member.

* * * * *